(12) United States Patent
Lu

(10) Patent No.: US 10,254,167 B2
(45) Date of Patent: Apr. 9, 2019

(54) METHOD FOR SORTING A LIGHT SOURCE

(71) Applicants: LITE-ON ELECTRONICS (GUANGZHOU) LIMITED, Guangzhou (CN); LITE-ON TECHNOLOGY CORP., Taipei (TW)

(72) Inventor: Yu-Kang Lu, Taipei (TW)

(73) Assignees: Lite-On Electronics (Guangzhou) Limited, Guangzhou (CN); Lite-On Technology Corp., Taipei (TW)

(*) Notice: Subject to any disclaimer, the term of this patent is extended or adjusted under 35 U.S.C. 154(b) by 875 days.

(21) Appl. No.: 13/936,387

(22) Filed: Jul. 8, 2013

(65) Prior Publication Data

US 2014/0025340 A1    Jan. 23, 2014

(30) Foreign Application Priority Data

Jul. 17, 2012    (CN) .......................... 2012 1 0247469

(51) Int. Cl.
| | |
|---|---|
| *G01J 3/46* | (2006.01) |
| *G01J 1/16* | (2006.01) |
| *G01J 3/50* | (2006.01) |
| *G01N 21/27* | (2006.01) |
| *G01J 1/42* | (2006.01) |

(52) U.S. Cl.
CPC ................ *G01J 3/463* (2013.01); *G01J 1/16* (2013.01); *G01J 3/505* (2013.01); *G01N 21/274* (2013.01); *G01J 2001/4252* (2013.01)

(58) Field of Classification Search
CPC ........................... H05B 33/0803; G01J 3/463
USPC .............. 702/127, 179, 183, 186, 188, 189; 315/151; 345/55; 348/645; 362/231
See application file for complete search history.

(56) References Cited

U.S. PATENT DOCUMENTS

| | | | | |
|---|---|---|---|---|
| 8,442,316 | B2* | 5/2013 | Bassi | ...................... G06T 5/008 345/55 |
| 2007/0242162 | A1* | 10/2007 | Gutta | ...................... G06T 7/408 348/645 |
| 2008/0013314 | A1* | 1/2008 | Ashdown | ........... H05B 33/0803 362/231 |
| 2009/0295839 | A1* | 12/2009 | Furukawa | ............ G09G 3/3413 345/690 |
| 2013/0264947 | A1* | 10/2013 | Ouderkirk | ........... H01L 25/0753 315/151 |

* cited by examiner

*Primary Examiner* — Manuel A Rivera Vargas
(74) *Attorney, Agent, or Firm* — Rosenberg, Klein & Lee

(57) ABSTRACT

A method for sorting a light source is to be implemented by a computer and includes configuring the computer to determine whether or not a to-be-sorted light source is different from a reference light source by comparing features of a curve associated with measured spectral data of the to-be-sorted light source, with features of a reference curve associated with reference spectral data of a reference light source.

18 Claims, 6 Drawing Sheets

METHOD FOR SORTING A LIGHT SOURCE

CROSS-REFERENCE TO RELATED APPLICATION

This application claims priority of Chinese Patent Application No. 201210247469.6, filed on Jul. 17, 2012.

BACKGROUND OF THE INVENTION

1. Field of the Invention

The invention relates to a sorting method, more particularly to a method for sorting a light source.

2. Description of the Related Art

In light source analysis, the CIE (Commission Internationale de l'éclairage) 1931 coordinates (referred to as CIE coordinates hereinafter) are generally adopted for defining a light color emitted from a light source. The CIE coordinates are usually represented in a form of (x, y), and each specific coordinate point (a, b) corresponds to a specific color. Moreover, a color which corresponds to a coordinate point (a, b) is similar to a color which corresponds to a coordinate point (a+Δx, b+Δy) proximate to the coordinate point (a, b). For example, pure white corresponds to a CIE coordinate point of (0.33, 0.33), so that a color which corresponds to a CIE coordinate point proximate to (0.33, 0.33) may be regarded as similar to pure white.

In addition, each specific light color corresponding to a specific CIE coordinate point (a, b) may be composed of different light components with respective wavelengths, that is, light sources which emit lights of different spectral compositions may emit a substantially same light color, and the light color corresponds to a substantially same CIE coordinate point. This characteristic is called metamerism of the CIE coordinate system. Therefore, in a condition that the CIE coordinates are adopted to analyze different light sources, when the light sources emit substantially the same light color which corresponds to substantially the same CIE coordinate point, the analyzed result may not be usable for determination as to whether the light sources have substantially the same spectral characteristic.

For instance, a white LED (light-emitting diode) package light source may be composed of a LED die in combination with appropriate fluorescent powder (for example, a blue LED die in combination with yellow fluorescent powder). Each of two blue LED dies, which emit the same light color, may be adopted in combination with a respective one of yellow fluorescent powders, which has a specific composition of compounds at a specific weight ratio, to constitute a white LED package light source that emits a substantially same white color. However, spectral characteristics of the white LED package light sources may be distinct from each other because of the different fluorescent powders used thereby. Therefore, even though the CIE coordinates may be utilized to analyze and define the light color emitted from the white LED package light source, the spectral characteristics of the white LED package light sources may not be obtained through the CIE coordinate analysis, and whether the white LED package light sources are constituted by the same combination of a LED die and fluorescent powder is unknown. In other words, it is insufficient to rely on CIE coordinates for analyzing and sorting different light sources.

SUMMARY OF THE INVENTION

Therefore, an object of the present invention is to provide a method for sorting light sources that emit a same light color with substantially the same color component composition (i.e., similar spectral characteristics) from a plurality of light sources.

An effect of the present invention resides in that, by virtue of analyzing the features of the curves associated with the measured spectral data of the to-be-sorted light source and the reference spectral data of the reference light source, respectively, the computer may determine whether the to-be-sorted light source and the reference light source are one of different from each other, emitting a same light color but with a substantially different color component composition, and emitting a same light color with substantially the same color component composition.

BRIEF DESCRIPTION OF THE DRAWINGS

Other features and advantages of the present invention will become apparent in the following detailed description of a preferred embodiment with reference to the accompanying drawings, of which.

DETAILED DESCRIPTION OF THE PREFERRED EMBODIMENT

Figure 1A:
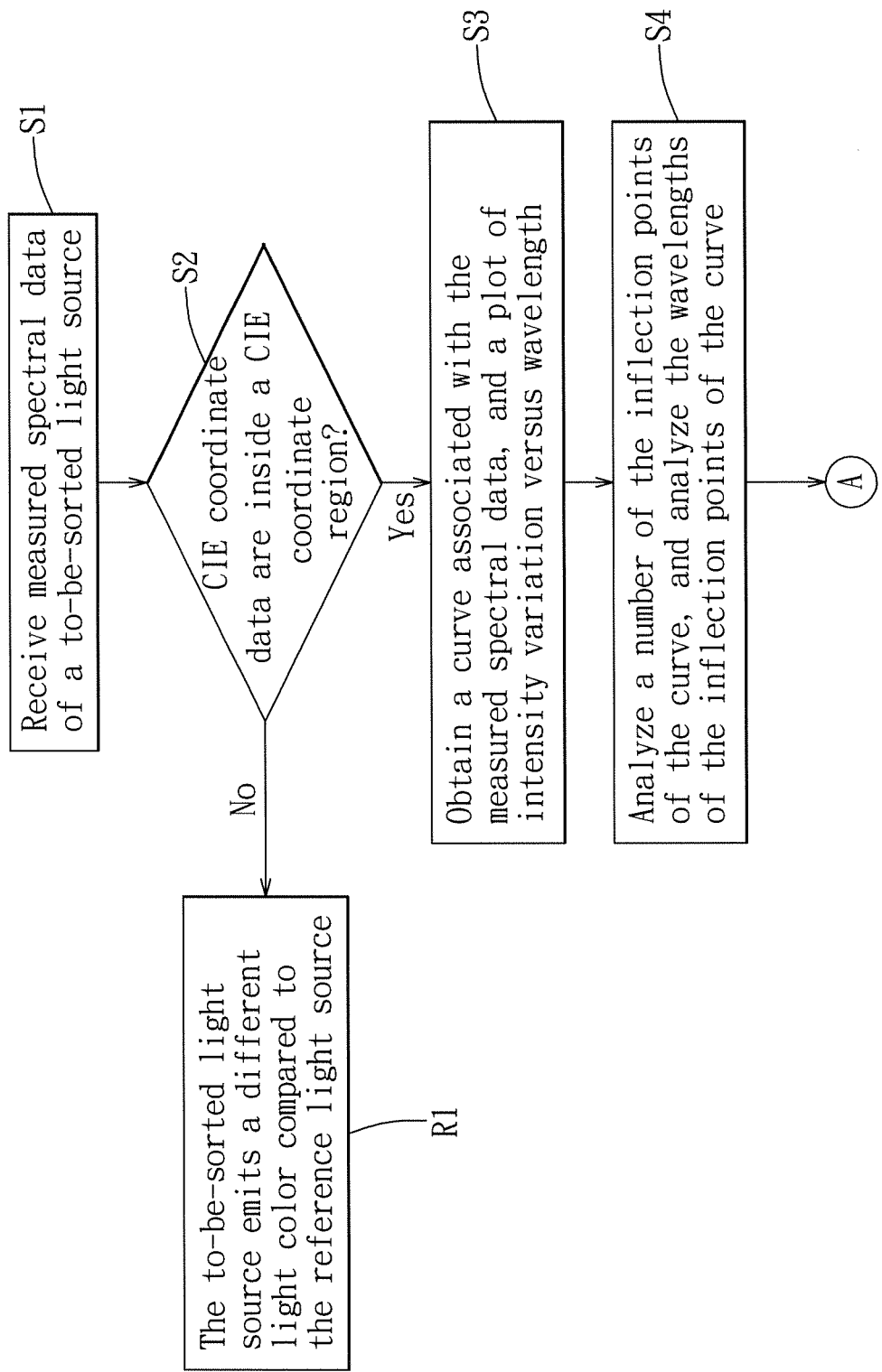
FIGS. 1A and 1B are a flowchart which illustrates a preferred embodiment of a method for sorting a light source according to the present invention.
Figure 1B:
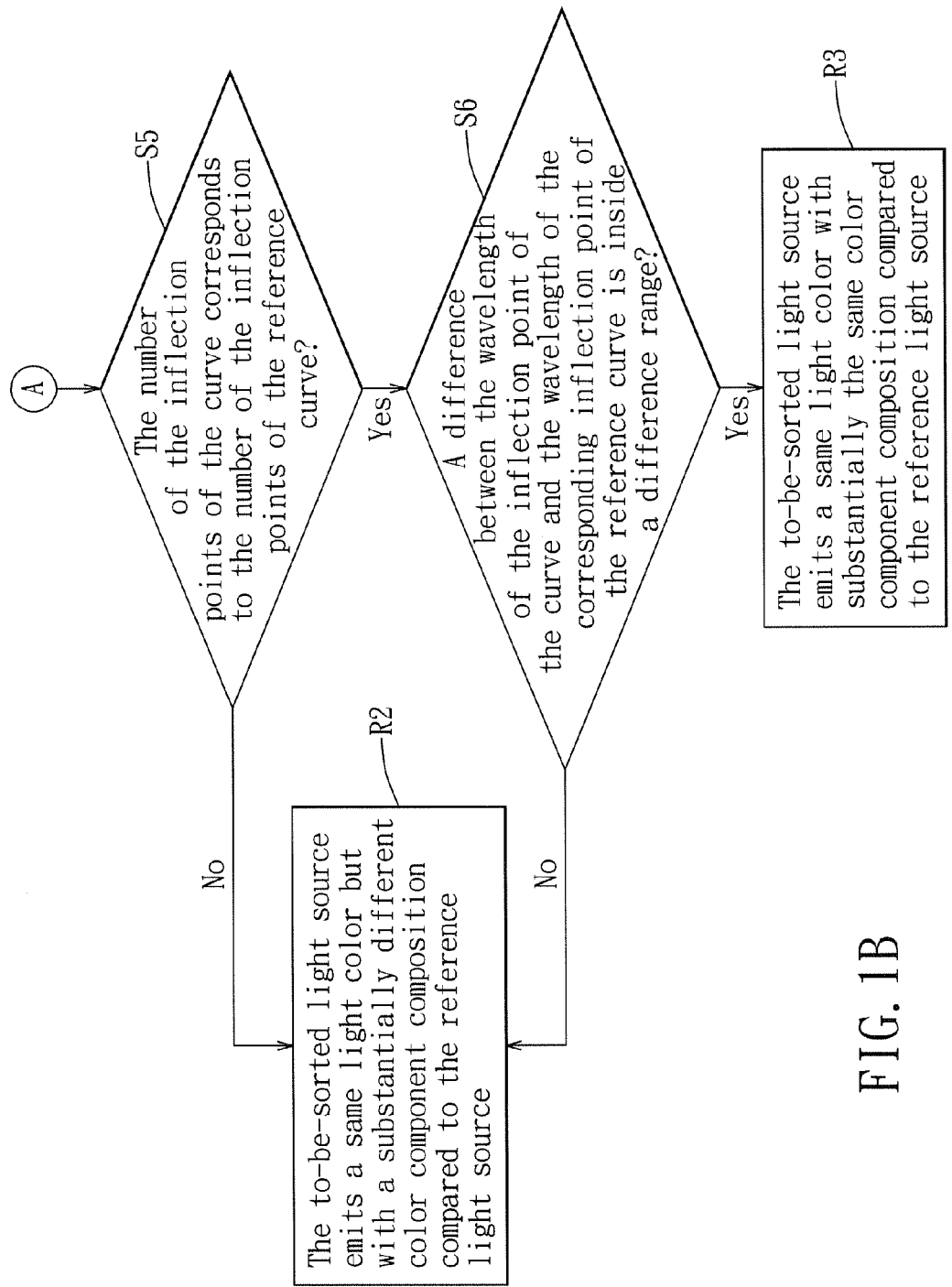

Referring to FIGS. 1A and 1B, a preferred embodiment of a method for sorting a light source according to the present invention is illustrated. In this embodiment, the method is applicable for analyzing and sorting a LED package, but the application thereof is not limited to such application. The method may be applied to other kinds of illumination light sources or illumination lamps. Detailed procedures associated with the method for sorting a light source will be described in the following paragraphs in conjunction with the accompanying drawings.

In this embodiment, the method for sorting a light source is to be implemented by a computer, and a spectral analysis apparatus is utilized to measure optical characteristics of a LED package so as to obtain measured spectral data (see Table 1). The measured spectral data is stored in the computer for future analysis and sorting procedures. The aforesaid spectral analysis apparatus is realized using an integrating sphere in combination with a LED optical & electric tester for measurement, but is not limited to the implementation disclosed herein.

Table 1 shows the measured spectral data of a to-be-sorted light source (i.e., the LED package). It should be noted that only a portion of the measured spectral data is listed in Table 1. The measured spectral data includes a plurality of measured data entries, each indicating a measured intensity of the to-be sorted light source at a corresponding wavelength within a predetermined wavelength interval. Each of the measured intensities has gone through a normalization process for the sake of comparative analysis among a plurality of measured spectral data. However, the measured intensities may be analyzed using original data thereof without going through the normalization process.

When measuring the LED package, the predetermined wavelength interval within which the LED package is to be measured by the spectral analysis apparatus is set to be between 380 nm and 780 nm via the computer, and the measured intensity of the to-be sorted light source is measured every wavelength variation $\Delta\lambda$, such as 1 nm. It is noted that the predetermined wavelength interval and the wavelength variation $\Delta\lambda$ may be changed according to different needs, and are not limited to the setup used herein.

TABLE 1

(The measured spectral data of the second type of light source)

| Wavelength $\lambda$ (nm) | Intensity (normalized) |
|---|---|
| 380 | 0.00000 |
| 381 | 0.00184 |
| . . . (abridged) | . . . (abridged) |
| 438 | 0.16956 |
| 439 | 0.18967 |
| 440 | 0.20988 |
| 441 | 0.22968 |
| 442 | 0.24866 |
| . . . (abridged) | . . . (abridged) |
| 779 | 0.02079 |
| 780 | 0.00000 |

Figure 2:
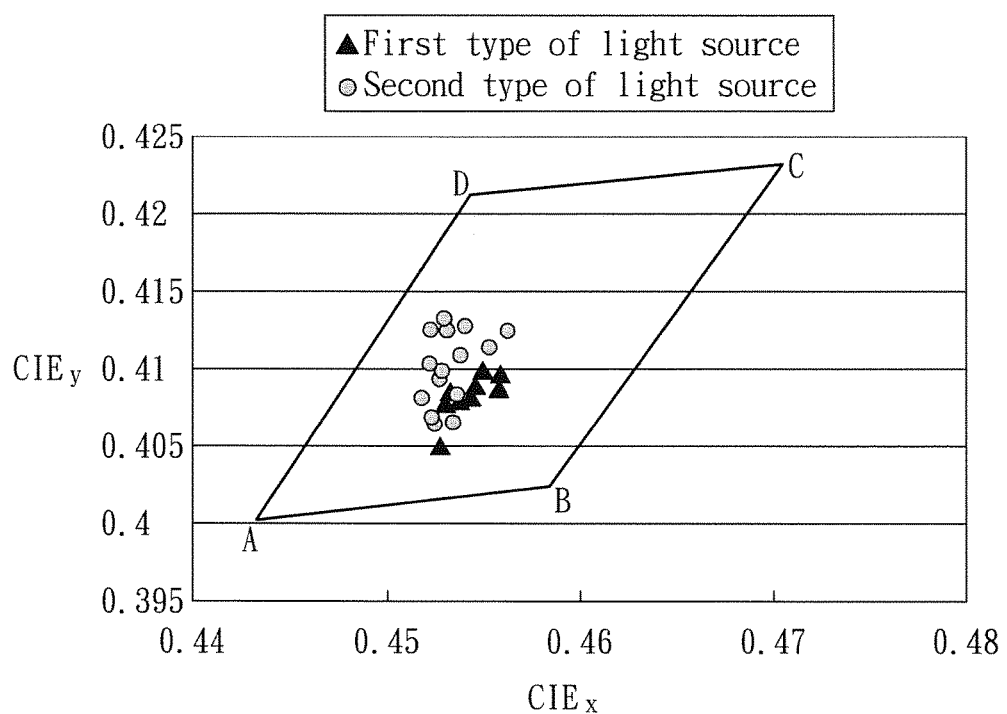
FIG. 2 is a CIE 1931 coordinate graph illustrating two types of LED package light sources which emit a substantially same light color.

Based on the above-mentioned data entries, the computer converts the measured spectral data into CIE coordinate data, that is, CIE 1931 coordinate data according to CIE15-2004 colorimetry, so as to indicate the measured spectral data on a CIE 1931 coordinate graph (see FIG. 2). In this embodiment, the CIE 1931 coordinate data is merely an example for conversion of the measured spectral data, and the coordinate system is not limited to the disclosure herein. As previously mentioned in the related art, LED dies which emit a substantially same light color may be combined with fluorescent powders having different specific composition of compounds at specific weight ratios to constitute LED package light sources that emit a substantially same light color. However, spectral characteristics of each of the LED package light sources may diverge as a result of the different fluorescent powders used thereby. Therefore, aside from analyzing light sources using the CIE coordinates, the present invention further determines whether or not the light sources emit a same light color with substantially the same color component composition by analyzing curves associated with measured spectral data of the light sources. Specifically, in a stage of CIE coordinate analysis, the present invention determines whether a to-be-sorted light source and a reference light source emit a substantially same light color, or emit different light colors. In a following stage of spectral curve feature analysis, the present invention determines whether the to-be-sorted light source and the reference light source have substantially the same spectral curve features or have different spectral curve features.

In the subsequent paragraphs, two types of LED package light sources are taken as examples for explanation of the preferred embodiment of the method for sorting a light source. The LED package light sources are formed with blue LED dies, which emit a substantially same light color and which have similar spectral characteristics, in combination with yellow fluorescent powders, which have different compositions of compounds, so as to emit white light. The compositions of the compounds of the yellow fluorescent power are F540+BR102C+BR102D and GAL540+BR102C+BR102D (all are compound codes for fluorescent powder), respectively. To facilitate explanation in the following paragraphs, the LED package light source which adopts the F540+BR102C+BR102D fluorescent powder is categorized as a first type of light source, and the LED package light source which adopts the GAL540+BR102C+BR102D fluorescent powder is categorized as a second type of light source.

Referring to FIG. 2, a CIE 1931 coordinate graph of a plurality of the first type of the LED package light sources (represented as black triangles) and a plurality of the second type of the LED package light sources (represented as grey circles) is illustrated. A trapezoid area cooperatively defined by coordinate points A (0.4433, 0.4003), B (0.4583, 0.4024), C (0.4703, 0.4230) and D (0.4542, 0.4210) is a predetermined CIE coordinate region associated with the first type of the LED package light sources. That is, the CIE coordinate data associated with reference spectral data of the first type of the LED package light sources are inside the predetermined CIE coordinate region. However, it is obvious from FIG. 2 that the CIE coordinate data associated with the measured spectral data of the second type of the LED package light sources are also inside the predetermined CIE coordinate region. In other words, the first type and the second type of the LED package light sources emit substantially the same light color and thus have the CIE coordinate data proximate to each other. Moreover, since it is obvious from distribution of the CIE coordinate data on the CIE 1931 coordinate graph that discriminating differences between light colors emitted from the LED package light sources by merely relying on human eyes is almost impossible, the first type and the second type of the LED package light sources may be sorted as light sources which emit a substantially same color. Therefore, in order to discriminate the first type of light source from the second type of light source which adopt different fluorescent powders with distinct compositions of compounds, the subsequent spectral curve feature analysis is required.

Referring to FIG. 1A to FIG. 4, the preferred embodiment of the method for sorting a LED package light source according to the present invention is illustrated hereinafter.

In step S1, the computer is configured to receive the measured spectral data of the to-be-sorted light source.

The measured spectral data of the to-be-sorted light source includes a plurality of the measured data entries, each indicating the measured intensity of the to-be sorted light source at the corresponding wavelength (see Table 1). Herein, the to-be-sorted light source belongs to the second type of light source. In subsequent steps, the measured spectral data of the to-be-sorted light source will be analyzed and compared with reference spectral data of a reference light source which are prestored in the computer. The reference light source belongs to the first type of light source, and the reference spectral data are listed in Table 2.

TABLE 2

(The reference spectral data of the first type of light source)

| Wavelength λ (nm) | Intensity (normalized) |
|---|---|
| 380 | 0.00000 |
| 381 | 0.00218 |
| ... (abridged) | ... (abridged) |
| 438 | 0.18062 |
| 439 | 0.20031 |
| 440 | 0.22073 |
| 441 | 0.24147 |
| 442 | 0.26194 |
| ... (abridged) | ... (abridged) |
| 779 | 0.02085 |
| 780 | 0.00000 |

In step S2, the computer is configured to convert the measured spectral data, and to determine whether CIE coordinate data associated with the measured spectral data are inside a CIE coordinate region associated with the reference light source.

The computer obtains the CIE coordinate data of the to-be-sorted light source through calculation based on the measured spectral data thereof, and determines whether the CIE coordinate data are inside or outside the predetermined CIE coordinate region associated with the reference spectral data of the reference light source, so as to determine whether the to-be-sorted light source emits a substantially same light color compared to the reference light source. When the CIE coordinate data associated with the measured spectral data of the to-be-sorted light source are inside the CIE coordinate region associated with the reference light source (see FIG. 2), it means that the to-be-sorted light source emits substantially the same light color compared to the reference light source, and the flow proceeds to step S3. On the other hand, when the CIE coordinate data of the to-be-sorted light source are outside the CIE coordinate region, the flow proceeds to step R1. In step R1, the computer is configured to determine that the to-be-sorted light source is different from the reference light source, i.e., the to-be-sorted light source emits a different light color compared to the reference light source.

It is noted that the CIE coordinate region associated with the reference light source may be adjusted depending on needs, and is not limited to the disclosed trapezoid area ABCD in this embodiment.

By virtue of steps S1 and S2, the preferred embodiment may fulfill the following procedure of the method according to the present invention:

configuring the computer to determine whether or not the to-be-sorted light source is different from the reference light source based on whether CIE coordinate data associated with the measured spectral data are inside or outside a CIE coordinate region associated with the reference light source.

In step S3, the computer is configured to obtain a curve associated with the measured spectral data of the to-be-sorted light source, and a plot of intensity variations of the measured data entries versus the wavelengths of the measured data entries. It is noted that the plot is a conversion from the curve associated with the measured spectral data of the to-be-sorted light source. Therefore, for the sake of brevity, the curve associated with the measured spectral data of the to-be-sorted light source is referred to as a spectral curve, and the plot of intensity variations of the measured data entries versus the wavelengths of the measured data entries is referred to as a converted spectral curve.

Figure 3:
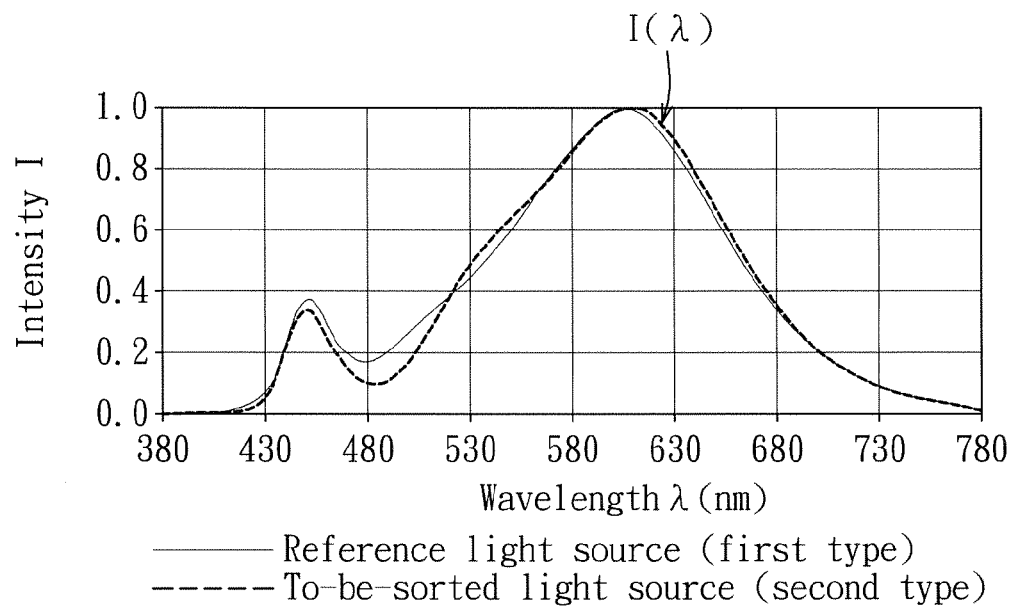
FIG. 3 illustrates curves (i.e., spectral curves) associated with spectral data of two types of LED package light sources which emit a same light color but with substantially different color component compositions.

FIG. 3 illustrates the curve which is depicted based on the measured spectral data of the to-be-sorted light source (Table 1) and a reference curve associated with reference spectral data of the reference light source (Table 2). A horizontal axis in FIG. 3 represents the wavelength in the unit of nanometer (nm), and a vertical axis in FIG. 3 represents the intensity that has been normalized and thus has no unit. The reference curve presented in solid line corresponds to the reference light source, i.e., the first type of light source. The curve presented in broken line corresponds to the to-be-sorted light source, i.e., the second type of light source.

As shown in FIG. 3, the reference curve and the curve associated with the measured spectral data have similar trends of spectral distribution, but features (especially bend features) of the two curves substantially diverge. Specifically, both of the reference curve and the curve associated with the measured spectral data have relatively small peaks at corresponding wavelengths proximate to 450 nm, and have relatively large peaks at corresponding wavelengths proximate to 610 nm. On the other hand, the reference curve and the curve associated with the measured spectral data have greater differences in bend features within a corresponding wavelength interval ranging from 450 nm to 580 nm. For each of the reference curve and the curve associated with the measured spectral data, the bend features include inflection points. Therefore, in the present invention, the inflection points of the reference curve and the curve associated with the measured spectral data are further analyzed by the computer for discriminating the differences in the bend features of the two curves, so as to determine whether or not the to-be-sorted light source is different from the reference light source. Accordingly, the computer is configured to convert the measured spectral data into converted spectral data for comparing the bend features of the curves. The converted spectral data indicate, for each of the measured data entries, the intensity variation of the to-be sorted light source at a corresponding wavelength.

In mathematical definition, an inflection point is a point on a curve at which the curve changes from concave upward to concave downward or changes from concave downward to concave upward. The above-mentioned definition may be interpreted in a manner that the inflection point is a transitioning coordinate point of bend features of the curve. Herein, the concave upward means that slope along the curve within a corresponding wavelength range gradually increases, and the concave downward means that slope along the curve within a corresponding wavelength range gradually decreases. Therefore, the inflection point may be regarded as the transitioning coordinate point at which the slope along the curve changes from increasing gradually to decreasing gradually or the transitioning coordinate point at which the slope along the curve changes from decreasing gradually to increasing gradually.

Accordingly, the slope of the reference curve and the curve associated with the measured spectral data may be defined as:

$$m = \frac{\Delta I}{\Delta \lambda}$$

wherein m represents the slope of one of the reference curve and the curve associated with the measured spectral data at a specific point thereon, I represents the intensity corresponding to the specific point on said one of the two curves, ΔI represents an intensity variation corresponding to the specific point on said one of the two curves, λ represents a wavelength corresponding to the specific point on said one of the two curve, and Δλ represents a wavelength variation corresponding to the specific point on said one of the two curves. For analyzing and explaining the bend features in the following paragraphs, a function I(λ) is introduced to represent that the intensity I is a function of the wavelength λ, i.e., said one of the reference curve and the curve associated with the measured spectral data is a graph of the function I(λ).

As mentioned above, for each of the reference light source and the to-be-sorted light source, the spectral data of the light source includes the plurality of data entries, each indicating the intensity of the light source which is measured every wavelength variation. That is, the wavelength variation Δλ of the curve associated with the spectral data may be regarded as a constant. Therefore, the slope m of said one of the reference curve and the curve associated with the measured spectral data (i.e., the spectral curve) is directly proportional to the intensity variation ΔI:

$$m \propto \Delta I$$

In other words, the inflection point may also be regarded as the transitioning coordinate point at which the intensity variation ΔI of the spectral curve changes from decreasing gradually to increasing gradually or the transitioning coordinate point at which the intensity variation ΔI of the spectral curve changes from decreasing gradually to increasing gradually. Therefore, by analyzing the intensity variations ΔI of the reference curve and the curve associated with the measured spectral data, the inflection points thereof may be obtained.

Figure 4:
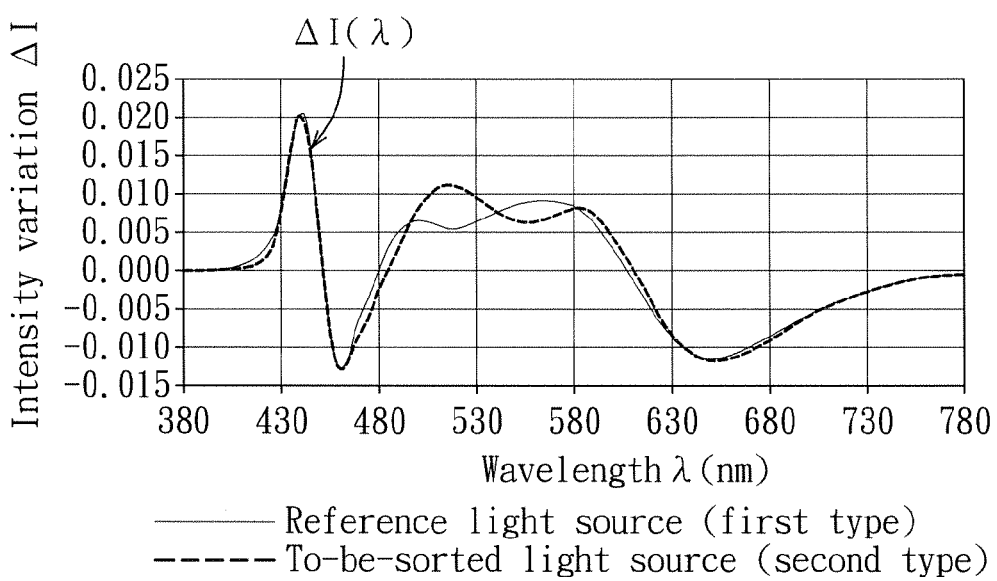
FIG. 4 illustrates plots (i.e., converted spectral curves), which are obtained by conversion of the curves depicted in FIG. 3, of intensity variation versus wavelength.

FIG. 4 illustrates plots of intensity variation versus the wavelength. The plots (i.e., converted spectral curves) may be obtained by conversion of the curves (i.e., spectral curve) depicted in FIG. 3. According to the converted spectral curves shown in FIG. 4, a variation tendency of the intensity variations ΔI of the reference curve and the curve associated with the measured spectral data shown in FIG. 3 may be known, so that the inflections points thereon may be obtained. In this way, the bend features of the curve associated with the measured spectral data, and the bend features of the reference curve may be further compared. A horizontal axis in FIG. 4 represents the wavelength in the unit of nanometer (nm), and a vertical axis in FIG. 4 represents the intensity variation that does not have any unit.

A manner for obtaining the converted spectral curves in FIG. 4 of the intensity variations of the measured data entries versus the wavelengths of the measured data entries is explained herein. A function ΔI(λ) is introduced to represent that the intensity variation ΔI is a function of the wavelength λ, i.e., each of the converted spectral curves in FIG. 4 is a graph of the function ΔI(λ). The relationship between the function ΔI(λ) and the function I(λ) is represented as:

$$\Delta I(\lambda) = I(\lambda) - I(\lambda - \Delta\lambda)$$

wherein an output of the function ΔI(λ) is the intensity variation ΔI corresponding to a specific wavelength λ, and an output of the function I(λ) is the intensity I corresponding to the specific wavelength λ.

Referring to Table 1, the to-be-sorted light source is taken as an example. The intensity of the to-be-sorted light source is measured every 1 nm, such that the wavelength variation Δλ is 1 nm. Moreover, the intensity of the to-be-sorted light source at a wavelength of 440 nm is 0.20988, such that I(440)=0.20988. The intensity of the to-be-sorted light source at a wavelength of 439 nm is 0.18967, such that I(439)=0.18967. Accordingly, the intensity variation ΔI (440) of the to-be-sorted light source at the wavelength of 440 nm may be computed as:

$$\Delta I(440) = I(440) - I(440 - 1)$$
$$= I(440) - I(439)$$
$$= 0.20988 - 0.18967$$
$$= 0.02021$$

In this way, the measured intensity of the to-be-sorted light source indicated in each of the measured data entries shown in Table 1 may be converted one by one into a corresponding intensity variation ΔI, so as to obtain the data shown in Table 3. Furthermore, the reference spectral data of the reference light source may also be converted in the same way into data shown in Table 4. Subsequently, the plot of intensity variation versus wavelength of the to-be-sorted light source shown in Table 3 is depicted in FIG. 4 with a broken line. Similarly, the plot of intensity variation versus wavelength of the reference light source shown in Table 4 is depicted in FIG. 4 with a solid line.

In one configuration of this embodiment, the relationship between the function ΔI(λ) and the function I(λ) may also be represented in the following manner for achieving substantially the same effect:

TABLE 3

(The wavelengths, the intensities and the intensity variations of the to-be-sorted light source)
ΔI(λ) = I(λ + Δλ) − I(λ)

| Wavelength λ | Intensity I | Intensity variation ΔI |
|---|---|---|
| 380 | 0.00000 | — |
| 381 | 0.00184 | 0.00184 |
| . . . (abridged) | . . . (abridged) | . . . (abridged) |
| 438 | 0.16956 | 0.01958 |
| 439 | 0.18967 | 0.02011 |
| 440 | 0.20988 | 0.02021 |
| 441 | 0.22968 | 0.01980 |
| 442 | 0.24866 | 0.01898 |
| . . . (abridged) | . . . (abridged) | . . . (abridged) |
| 779 | 0.02079 | −0.00053 |
| 780 | 0.00000 | — |

TABLE 4

(The wavelengths, the intensities and the intensity variations of the reference light source)

| Wavelength λ | Intensity I | Intensity variation ΔI |
|---|---|---|
| 380 | 0.00000 | — |
| 381 | 0.00218 | 0.00218 |
| . . . (abridged) | . . . (abridged) | . . . (abridged) |
| 438 | 0.18062 | 0.01867 |
| 439 | 0.20031 | 0.01969 |

TABLE 4-continued (The wavelengths, the intensities and the intensity variations of the reference light source)

| Wavelength λ | Intensity I | Intensity variation ΔI |
|---|---|---|
| 440 | 0.22073 | 0.02042 |
| 441 | 0.24147 | 0.02074 |
| 442 | 0.26194 | 0.02047 |
| ... (abridged) | ... (abridged) | ... (abridged) |
| 779 | 0.02085 | −0.00054 |
| 780 | 0.00000 | — |

By virtue of step S3, the preferred embodiment may fulfill the following procedure of the method according to the present invention:

configuring the computer to find the inflection points of the curve associated with the measured spectral data, including calculating an intensity variation of each of the measured data entries, and finding the inflection points with reference to the measured data entries and the intensity variations calculated for the measured data entries.

In step S4, the computer is configured to analyze a number of the inflection points of the curve associated with the measured spectral data, and to analyze the wavelengths of the inflection points of the curve associated with the measured spectral data, according to the plot of the intensity variation versus the wavelength.

Based on the aforementioned relationship between the function ΔI(λ) and the function I(λ), the curve associated with the measured spectral data, and the plot of intensity variation versus the wavelength obtained in step S3 have the following characteristics. The wavelengths of the inflection points of the curve (i.e., spectral curve) in FIG. 3 correspond respectively to wavelengths of peaks of the plot (i.e., converted spectral curve) in FIG. 4 where the intensity variation ΔI changes from increasing gradually to decreasing gradually, or correspond respectively to wavelengths of valleys of the converted spectral curve in FIG. 4 where the intensity variation ΔI changes from decreasing gradually to increasing gradually.

Figure 5:
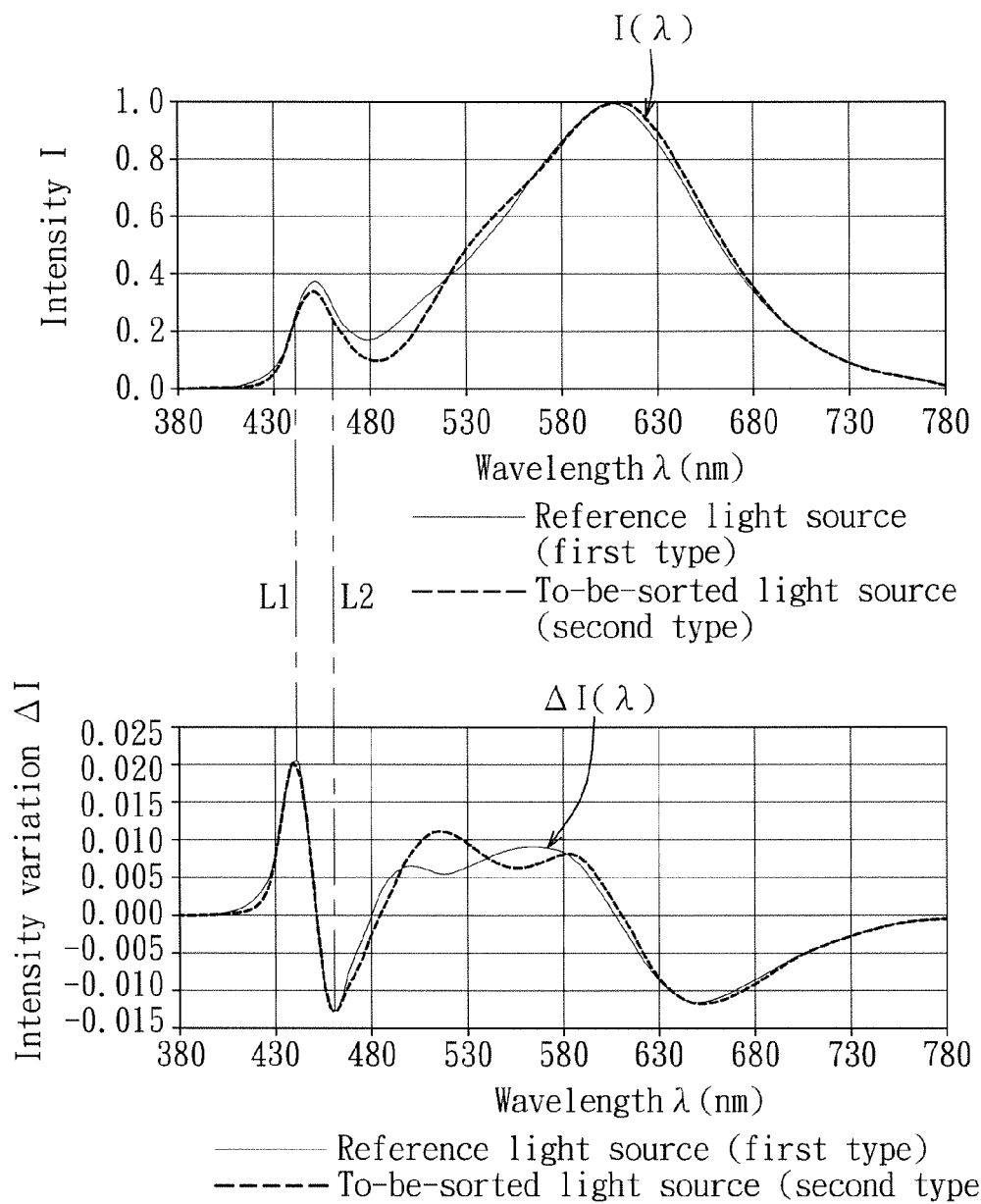
FIG. 5 illustrates a correspondence relationship between the spectral curves depicted in FIG. 3 and the converted spectral curves depicted in FIG. 4.

Referring to FIG. 5, the top half of the figure corresponds to FIG. 3 and the bottom half of the figure corresponds to FIG. 4, so as to illustrate correspondence relationship between the inflection points of the spectral curve, and the peaks and valleys of the converted spectral curve. With respect to a reference line L1, a wavelength of a first peak on the plot of the function ΔI(λ) (i.e., the converted spectral curve) corresponds to a wavelength of a first inflection point of the curve of the function I(λ). Similarly, with respect to a reference line L2, a wavelength of a first valley on the plot of the function ΔI(λ) corresponds to a wavelength of a second inflection point of the curve of the function I(λ). In other words, the inflection points of the curve associated with the measured spectral data correspond respectively to the peaks and the valleys of the plot of the intensity variations of the measured data entries versus the wavelengths of the measured data entries. Even though the computer is incapable of obtaining coordinate points of the inflection points on the spectral curves directly from the measured spectral data of the to-be-sorted light source and the reference spectral data of the reference light source, the computer is able to indirectly obtain the inflection points on the spectral curves by means of analyzing the wavelengths of the peaks and the valleys of the converted spectral curve. Therefore, the computer is configured to compare the bend features of the curve associated with the measured spectral data, with the bend features of the reference curve to determine whether or not the to-be-sorted light source is different from the reference light source. Detailed analysis is provided below.

TABLE 5

(Coordinate points of the peaks and valleys of the plot of intensity variation versus wavelength, wavelengths corresponding to the peaks and the valleys, and coordinate points of the inflection points on the curve associated with the measured spectral data of the to-be-sorted light source)

| Coordinate point of peaks and valleys of the converted spectral curve | Wavelengths corresponding to peaks and valleys | Coordinate point of inflection points of the spectral curve |
|---|---|---|
| First peak (440, 0.02022) | First peak 440 nm | First inflection point (440, 0.20988) |
| First valley (460, −0.01269) | First valley 460 nm | Second inflection point (460, 0.25405) |
| Second peak (516, 0.01121) | Second peak 516 nm | Third inflection point (516, 0.32777) |
| Second valley (556, 0.00628) | Second valley 556 nm | Fourth inflection point (556, 0.66977) |
| Third peak (580, 0.00827) | Third peak 580 nm | Fifth inflection point (580, 0.84316) |
| Third valley (651, −0.01198) | Third valley 651 nm | Sixth inflection point (651, 0.67904) |

TABLE 6

(Coordinate points of the peaks and valleys of the plot (i.e. the converted spectral curve) of intensity variation versus wavelength, wavelengths corresponding to the peaks and the valleys, and coordinate points of the inflection points on the reference curve associated with the reference spectral data of the reference light source)

| Coordinate point of peaks and valleys of the converted spectral curve | Wavelengths corresponding to peaks and valleys | Coordinate point of inflection points of the spectral curve |
|---|---|---|
| First peak (441, 0.02074) | First peak 441 nm | First inflection point (441, 0.24147) |
| First valley (460, −0.01321) | First valley 460 nm | Second inflection point (460, 0.29651) |
| Second peak (499, 0.00658) | Second peak 499 nm | Third inflection point (499, 0.25370) |
| Second valley (517, 0.00560) | Second valley 517 nm | Fourth inflection point (517, 0.36289) |
| Third peak (563, 0.00915) | Third peak 563 nm | Fifth inflection point (563, 0.70997) |
| Third valley (647, −0.01169) | Third valley 647 nm | Sixth inflection point (647, 0.69085) |

Referring to FIG. 3 and FIG. 4 in combination with Table 5, according to the aforementioned analysis scheme, the coordinate points of the first, second and third peaks of the converted spectral curve of intensity variation versus wavelength of the to-be-sorted light source are (440, 0.02022), (516, 0.01121) and (580, 0.00827), respectively. The corresponding wavelengths thereof are 440 nm, 516 nm and 580 nm, respectively, and are referred to as a first peak wavelength ($\bar{\lambda}_{peak-1}$), a second peak wavelength ($\bar{\lambda}_{peak-2}$) and a third peak wavelength ($\bar{\lambda}_{peak-3}$), respectively.

Accordingly, the wavelengths of the first, third and fifth inflection points on the spectral curve depicted in FIG. 3 are 440 nm, 516 nm and 580 nm, respectively, such that the coordinate points thereof are (440, 0.20988), (516, 0.32777) and (580, 0.84316), respectively.

Moreover, the coordinate points of the first, second and third valleys of the converted spectral curve of the to-be-sorted light source depicted in FIG. 4 are (460, −0.01269), (556, 0.00628) and (651, −0.01198), respectively. The corresponding wavelengths thereof are 460 nm, 556 nm and 651 nm, respectively, and are referred to as a first valley wavelength ($\bar{\lambda}_{valley-1}$), a second valley wavelength ($\bar{\lambda}_{valley-2}$) and a third valley wavelength ($\bar{\lambda}_{valley-3}$), respectively.

Accordingly, the wavelengths of the second, fourth and sixth inflection points on the spectral curve depicted in FIG. 3 are 460 nm, 556 nm and 651 nm, respectively, such that the coordinate points thereof are (460, 0.25405), (556, 0.66977) and (651, 0.67904), respectively.

In the same manner, referring to FIG. 3 and FIG. 4 in combination with Table 6, the coordinate points of the first, second and third peaks of the converted spectral curve of intensity variation versus wavelength of the reference light source are (441, 0.02074), (499, 0.00658) and (563, 0.00915), respectively. The corresponding wavelengths thereof are 441 nm, 499 nm and 563 nm, respectively. Accordingly, the coordinate points of the first, third and fifth inflection points on the reference curve of the reference light source depicted in FIG. 3 are (441, 0.24147), (499, 0.25370) and (563, 0.70997), respectively.

Moreover, the coordinate points of the first, second and third valleys of the converted spectral curve of the reference light source depicted in FIG. 4 are (460, −0.01321), (517, 0.00560) and (647, −0.01169), respectively. The corresponding wavelengths thereof are 460 nm, 517 nm and 647 nm, respectively. Accordingly, the coordinate points of the second, fourth and sixth inflection points on the reference curve of the reference light source depicted in FIG. 3 are (460, 0.29651), (517, 0.36289) and (647, 0.69085), respectively.

As a result, the spectral curve of the to-be-sorted light source in FIG. 3 has six of the inflection points, and the wavelengths corresponding to the inflection points are 440 nm, 460 nm, 516 nm, 556 nm, 580 nm and 651 nm, respectively.

Similarly, the reference curve of the reference light source in FIG. 3 also has six of the inflection points, and the wavelengths corresponding to the inflection points are 441 nm, 460 nm, 499 nm, 517 nm, 563 nm and 647 nm, respectively.

At this point, the computer has obtained the number of the inflection points of the curves associated with the to-be-sorted light source and the reference light source, and the wavelengths of the inflection points.

In step S5, the computer is configured to determine whether or not the number of the inflection points of the curve associated with the measured spectral data corresponds to the number of the inflection points of the reference curve.

When a result of the determination made in step S5 is affirmative, the flow proceeds to step S6. When the result of the determination made in step S5 is negative, the flow proceeds to step R2. In step R2, the computer is configured to determine that the to-be-sorted light source emits a same light color but with a substantially different color component composition compared to the reference light source. This means that the CIE coordinate data of the to-be-sorted light source are proximate to the CIE coordinate data of the reference light source or are inside the CIE coordinate region associated with the reference light source, but the features of the reference curve diverge from the features of the curve associated with the measured spectral data of the to-be-sorted light source, such that the computer determines that the to-be-sorted light source is different from the reference light source. According to a result of the analysis in step S4, the curves associated with the to-be-sorted light source and the reference light source have the same number of the inflection points (six), such that step S6 is performed.

In step S6, when it is determined in step S5 that the number of the inflection points of the curve associated with the measured spectral data corresponds to the number of the inflection points of the reference curve, the computer is further configured to determine whether a difference between the wavelength of any one of the inflection points of the curve associated with the measured spectral data and the wavelength of the corresponding one of the inflection points of the reference curve is inside a predetermined difference range.

When a result of the determination made in step S6 is affirmative, the flow proceeds to step R3. In step R3, the computer is configured to determine that the to-be-sorted light source emits a same light color with substantially the same color component composition compared to the reference light source. This means that the CIE coordinate data of the to-be-sorted light source are proximate to the CIE coordinate data of the reference light source or are inside the CIE coordinate region associated with the reference light source, and the features of the reference curve are identical (or similar) to the features of the curve associated with the measured spectral data of the to-be-sorted light source, such that the computer determines that the to-be-sorted light source and the reference light source belong to the same type of light source. When the result of the determination made in step S6 is negative, the flow proceeds to R2. In step R2, the computer is configured to determine that the to-be-sorted light source emits a same light color but with a substantially different color component composition compared to the reference light source.

TABLE 7

(Data table for the to-be-sorted light source and the reference light source which emit a same light color but with a substantially different color component composition)

| | First inflection point | Second inflection point | Third inflection point | Fourth inflection point | Fifth inflection point | Sixth inflection point |
|---|---|---|---|---|---|---|
| Reference light source (First type) | 441 | 460 | 499 | 517 | 563 | 647 |
| To-be-sorted light source (Second type) | 440 | 460 | 516 | 556 | 580 | 651 |
| Wavelength difference | 1 | 0 | 17 | 39 | 17 | 4 |
| Difference range | 15 | 15 | 10 | 10 | 10 | 10 |
| Result | Pass | Pass | Fail | Fail | Fail | Fail |

Referring to Table 7, the data table records the results of the analysis of the to-be-sorted light source and the reference light source made by the computer in step S4, and the result of the determination made in step S6. It is noted that an absolute value of the difference between the wavelength of any one of the inflection points of the curve associated with the measured spectral data and the wavelength of the corresponding one of the inflection points of the reference curve is defined as a wavelength difference of inflection point $\overline{\lambda}_{difference}$. Moreover, the predetermined difference range $\overline{\lambda}_{spec}$ (i.e., a specification of wavelength difference) is defined for estimation of a degree of the wavelength difference of inflection points, and is adjustable according to different needs.

When the wavelength difference of inflection points is smaller than the predetermined difference range ($\overline{\lambda}_{difference}<\overline{\lambda}_{spec}$), said one of the inflection points of the spectral curve of the to-be-sorted light source is determined to pass a criterion as to whether the wavelength difference of inflection points is inside the predetermined difference range. That is, the wavelength of said one of the inflection points of the curve associated with the measured spectral data (i.e., the spectral curve) is close to the wavelength of the corresponding one of the inflection points of the reference curve. On the other hand, when the wavelength difference of inflection points is greater than or equal to the predetermined difference range ($\overline{\lambda}_{difference}\geq\overline{\lambda}_{spec}$), said one of the inflection points of the spectral curve of the to-be-sorted light source is determined to fail the criterion. That is, the wavelength of said one of the inflection points of the curve associated with the measured spectral data substantially diverges from the wavelength of the corresponding one of the inflection points of the reference curve.

For example, the wavelength difference of the first inflection points is an absolute value of a difference between the wavelength of the first inflection point of the spectral curve of the to-be-sorted light source and the wavelength of the first inflection point of the reference curve, and may be computed as:

|440−441|=1

In this way, the wavelength difference of other inflection points in Table 7 may be obtained. The wavelength difference of the first inflection points is smaller than the predetermined difference range (1<15), such that the first inflection point of the spectral curve of the to-be-sorted light source passes the criterion. Further, the aforesaid content may be comprehended as that as long as the wavelength of the first inflection point of the spectral curve of the to-be-sorted light source corresponds to a range of 426-546 nm (441 nm±15 nm), the criterion is passed.

Moreover, the wavelength difference of the third inflection points is greater than a predetermined difference range associated with the third inflection points (17>10), such that the third inflection point of the spectral curve of the to-be-sorted light source does not pass the criterion. That is, a difference between the wavelength of the third inflection point of the curve associated with the measured spectral data and the wavelength of the third inflection point of the reference curve is outside the predetermined difference range.

Accordingly, by analyzing one by one the inflection points of the curve associated with the measured spectral data of the to-be-sorted light source, three of the inflection points pass the criterion while the other three fail the same. Therefore, the computer determines that the to-be-sorted light source emits a same light color but with a substantially different color component composition compared to the reference light source in step S6.

Finally, by means of the method for sorting a light source according to the present invention, the spectral characteristics of the to-be-sorted light source and the reference light source may be analyzed, so as to determine that these two light sources emit a same light color but with a substantially different color component composition. Therefore, it may be concluded that the fluorescent powder used in the LED package of the to-be-sorted light source is different from the fluorescent powder used in the LED package of the reference light source.

By virtue of the steps mentioned above, the preferred embodiment may fulfill the following procedure of the method according to the present invention:

configuring the computer to determine whether or not a to-be-sorted light source is different from a reference light source by comparing features of a curve associated with measured spectral data of the to-be-sorted light source, with features of a reference curve associated with reference spectral data of a reference light source.

It is noted that the predetermined difference range may be adjusted according to different types of light sources and requirements, and is not limited to the disclosure in this embodiment. Moreover, as long as any one of the inflection points does not pass the criterion of the corresponding difference range, the result of the determination made in step S6 associated with the to-be-sorted light source is negative. In addition, the criterion of step S6 may be configured in the following manner. When the wavelength difference of inflection points is smaller than or equal to the predetermined difference range ($\overline{\lambda}_{difference}\leq\overline{\lambda}_{spec}$), said one of the inflection points of the spectral curve of the to-be-sorted light source is determined to pass a criterion as to whether the wavelength difference of inflection points is inside the predetermined difference range. When the wavelength difference of inflection points is greater than the predetermined difference range ($\overline{\lambda}_{difference}>\overline{\lambda}_{spec}$) said one of the inflection points of the spectral curve of the to-be-sorted light source is determined to fail the criterion.

Referring to FIGS. 1A, 1B, 2, 6 and 7, a condition that the method of the present invention is used to sort light sources which emit a same light color with substantially the same color component composition (i.e., both belong to the first type of light source) is explained.

Figure 6:
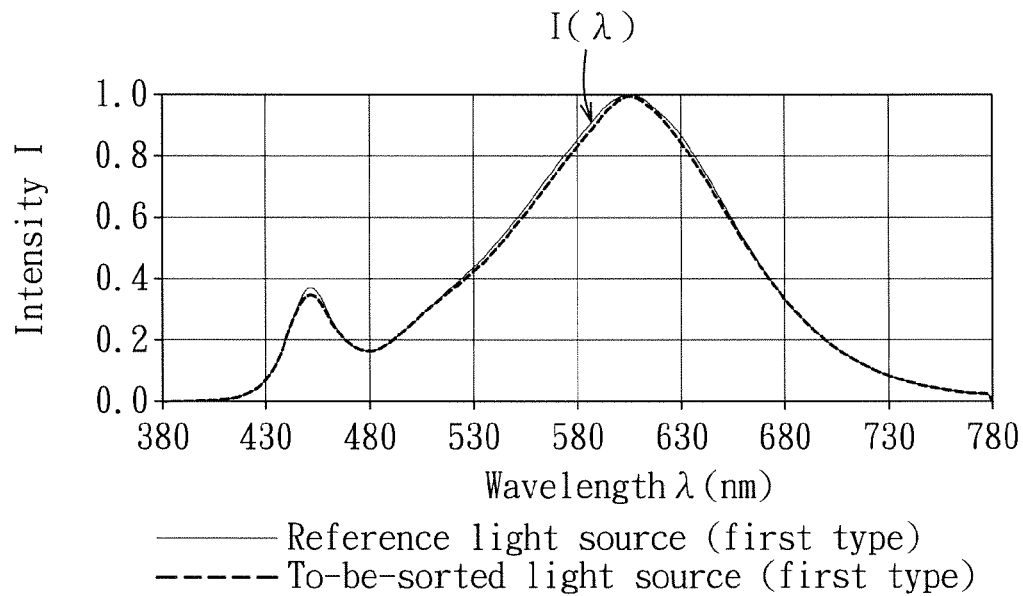
FIG. 6 is illustrates spectral curves associated with spectral data of two LED package light sources which emit a same light color with substantially the same color component composition.
Figure 7:
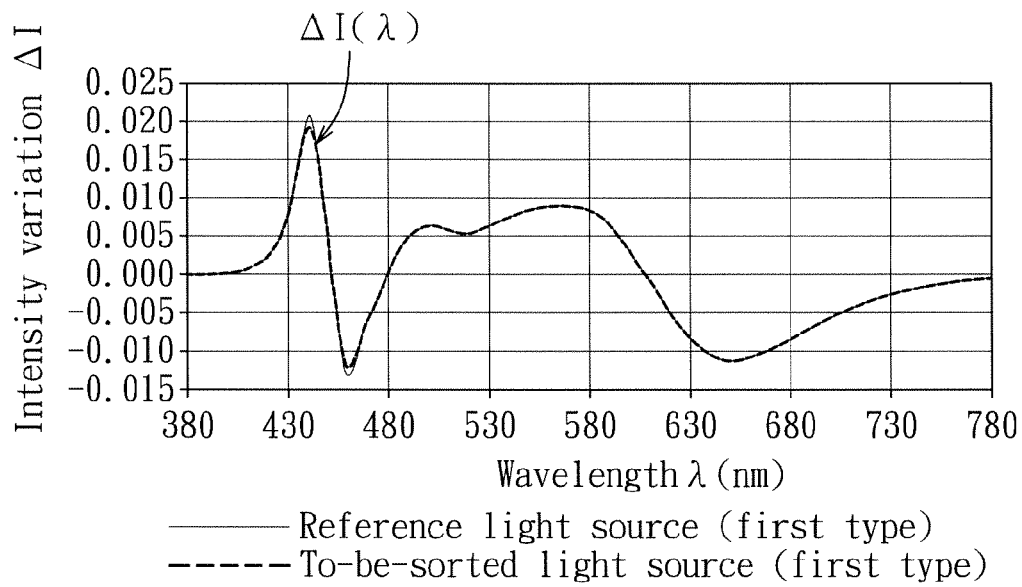
FIG. 7 illustrates converted spectral curves which are obtained by conversion of the curves depicted in FIG. 6.

Two curves associated with spectral data of two LED package light sources which emit a same light color with substantially the same color component composition are illustrated in FIG. 6. The curve associated with the measured spectral data of the to-be-sorted light source is presented in a broken line, and the reference curve associated with the reference spectral data of the reference light source is presented in a solid line. FIG. 7 illustrates plots (i.e., the converted spectral curves) of intensity variation versus wavelength which are obtained by conversion of the curves depicted in FIG. 6. The procedure for converting the spectral curve associated the measured spectral data into the converted spectral curve has been explained in the aforesaid steps S1-S6, and thus a description thereof is not repeated herein.

TABLE 8

(Data table for the to-be-sorted light source and the reference light source which emit a same light color with substantially the same color component composition)

| | First inflection point | Second inflection point | Third inflection point | Fourth inflection point | Fifth inflection point | Sixth inflection point |
|---|---|---|---|---|---|---|
| Reference light source (First type) | 441 | 460 | 499 | 517 | 563 | 647 |

TABLE 8-continued (Data table for the to-be-sorted light source and the reference light source which emit a same light color with substantially the same color component composition)

|  | First inflection point | Second inflection point | Third inflection point | Fourth inflection point | Fifth inflection point | Sixth inflection point |
|---|---|---|---|---|---|---|
| To-be-sorted light source (First type) | 441 | 460 | 502 | 514 | 566 | 649 |
| Wavelength difference | 0 | 0 | 3 | 3 | 3 | 2 |
| Difference range | 15 | 15 | 10 | 10 | 10 | 10 |
| Result | Pass | Pass | Pass | Pass | Pass | Pass |

Table 8 is a data table which records analytical results of the spectral curves and the converted spectral curves of the to-be-sorted light source and the reference light source. It is obvious from FIG. 2 that the CIE coordinate data associated with the measured spectral data of the to-be-sorted light source are inside the CIE coordinate region associated with the reference light source, such that a result of the determination made in step S2 is affirmative. Subsequently, it is obvious from Table 8 that both the to-be-sorted light source and the reference light source have six inflection points, so that the result of the determination made in step S5 by the computer is affirmative. Further, since the difference between the wavelength of any one of the six inflection points of the curve associated with the measured spectral data and the wavelength of the corresponding one of the inflection points of the reference curve is inside the corresponding predetermined difference range, the result of the determination made in step S6 by the computer is affirmative, and the flow proceeds to step R3. Finally, the computer determines that the to-be-sorted light source emits the same light color with substantially the same color component composition compared to the reference light source, that is the features of the spectral curves of the to-be-sorted light source and the reference light source are similar. Therefore, it may be concluded that the same fluorescent powder is used in both light sources.

To sum up, by the method for sorting a light source according to the present invention, a determination as to whether the to-be-sorted light source emits a different light color compared to the reference light source can be made, and subsequently a determination as to whether the to-be-sorted light source emits a same light color with substantially the same color component composition compared to the reference light source may be further made. In practice, a LED package whose composition of fluorescent powder used therein is known may be set as the reference light source. By applying the method of the present invention to LED packages whose composition of fluorescent powder used therein is unknown, the LED package which emits a same light color with substantially the same color component composition compared to the reference light source (i.e., the LED package using the same fluorescent powder and with a similar curve associated with spectral data) may be sorted out. Furthermore, the method according to the present invention may perform the CIE coordinate analysis and the spectral curve feature analysis on different kinds of light sources, such that the present invention is applicable to analyzing and sorting light sources other than LED packages.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for discriminating between light sources generating substantially similar light yet having different packaging, the method comprising:
   (A) measuring optical characteristics of a first light emitted by a to-be-sorted light source packaged using an unidentified composition of compounds to capture measured spectral data therefor, and converting the measured spectral data into color-defining coordinate data form, the measurement including capture of at least one wavelength parameter and at least one intensity parameter corresponding to the wavelength parameter;
   (B) discriminating the to-be-sorted light source from a reference light source in composite light color based on whether the color-defining coordinate data representing the measured spectral data are inside or outside a predefined color-defining coordinate region characteristic of a second light emitted by the reference light source; and
   (C) further discriminating the to-be-sorted light source from the reference light source in packaging composition despite substantial similarity in composite light color respectfully output thereby, the to-be-sorted light source being discriminated in spectral content by comparing bend features of a to-be-sorted spectral curve generated from the measured spectral data of the to-be-sorted light source and a reference spectral curve generated from reference spectral data of the reference light source, with respect to a predetermined difference range, the bend features including at least one inflection point,
   the to-be-sorted light source thereby discriminated from the reference light source based on packaging using differing compositions of compounds regardless of substantial similarity in composite light color respectively output from the to-be-sorted light source and the reference light source.

2. The method as claimed in claim 1, wherein, for each of the reference curve and the curve associated with the measured spectral data, the bend features include a plurality of inflection points, each of the inflection points indicating a point at which the curve changes between upward or downward orientations of concavity.

3. The method as claimed in claim 2, wherein operation (C) includes determining whether or not the to-be-sorted light source is different from the reference light source by comparing a number of the inflection points of the curve associated with the measured spectral data, with a number of the inflection points of the reference curve.

4. The method as claimed in claim 3, wherein operation (C) includes determining that the to-be-sorted light source emits a same light color but with a substantially different color component composition compared to the reference light source when the number of the inflection points of the curve associated with the measured spectral data is different from the number of the inflection points of the reference curve.

5. The method as claimed in claim 2, wherein operation (C) includes determining whether or not the to-be-sorted light source is different from the reference light source by further comparing wavelengths of the inflection points of the curve associated with the measured spectral data, with wavelengths of the inflection points of the reference curve.

6. The method as claimed in claim 5, wherein operation (C) includes determining whether or not a difference between the wavelength of any one of the inflection points of the curve associated with the measured spectral data and the wavelength of a corresponding one of the inflection points of the reference curve is inside or outside a predetermined difference range.

7. The method as claimed in claim 6, wherein-operation (C) includes determining that the to-be-sorted light source emits a same light color with substantially the same color component composition compared to the reference light source when the number of the inflection points of the curve associated with the measured spectral data corresponds to the number of the inflection points of the reference curve and when the difference between the wavelength of any one of the inflection points of the curve associated with the measured spectral data and the wavelength of the corresponding one of the inflection points of the reference curve is inside the predetermined difference range.

8. The method as claimed in claim 6, wherein operation (C) includes determining that the to-be-sorted light source emits a same light color but with a substantially different color component composition compared to the reference light source when the number of the inflection points of the curve associated with the measured spectral data corresponds to the number of the inflection points of the reference curve and when the difference between the wavelength of any one of the inflection points of the curve associated with the measured spectral data and the wavelength of the corresponding one of the inflection points of the reference curve is outside the predetermined difference range.

9. The method as claimed in claim 2,
wherein the measured spectral data includes a plurality of measured data entries, each indicating a measured intensity of the to-be-sorted light source at a corresponding wavelength, and
wherein operation (C) includes finding the inflection points of the curve associated with the measured spectral data, including calculating an intensity variation of each of the measured data entries, and finding the inflection points with reference to the measured data entries and the intensity variations calculated for the measured data entries.

10. The method as claimed in claim 9, wherein the inflection points of the curve associated with the measured spectral data correspond respectively to peaks and valleys of a plot of the intensity variations of the measured data entries versus the wavelengths of the measured data entries.

11. The method as claimed in claim 1, wherein, in operation (B), the measured spectral data includes a plurality of measured data entries, each measured data entry indicating a measured intensity of the to-be-sorted light source at a corresponding wavelength.

12. The method as claimed in claim 11, wherein operation (B) includes converting the measured data entries into the color-defining coordinate data according to a Commission Internationale de L'éclairage (CIE) 15 year 2004 colorimetry standard.

13. The method as claimed in claim 12, wherein the color-defining coordinate data is of a Commission Internationale de L'éclairage (CIE) year 1931 color space form.

14. The method as claimed in claim 1, further comprising:
proceeding to operation (C) only when the color-defining coordinate data associated with the measured spectral data are inside the color-defining coordinate region associated with the reference light source.

15. The method as claimed in claim 1, wherein operation (B) includes determining that the to-be-sorted light source emits a different light color compared to the reference light source when the color-defining coordinate data associated with the measured spectral data are outside the color-defining coordinate region associated with the reference light source.

16. The method as claimed in claim 1, wherein operation (B) includes determining that the to-be-sorted light source emits a same light color compared to the reference light source when the color-defining coordinate data associated with the measured spectral data are inside the color-defining coordinate region associated with the reference light source.

17. The method as claimed in claim 1, wherein operation (C) includes converting the measured spectral data into converted spectral data for comparing the bend features of the curves, the measured spectral data includes a plurality of measured data entries, each indicating a measured intensity of the to-be sorted light source at a corresponding wavelength, the converted spectral data indicating, for each of the measured data entries, an intensity variation of the to-be sorted light source at a corresponding wavelength.

18. A method for discriminating between light sources generating substantially similar light yet having different packaging, based on the light emitted respectively thereby, the method comprising:
measuring optical characteristics of a first light emitted by a to-be-sorted light source packaged using an unidentified composition of compounds to capture measured spectral data therefor, and converting the measured spectral data into color-defining coordinate data form, the measurement including capture of at least one wavelength parameter and at least one intensity parameter corresponding to the wavelength parameter; and
discriminating the to-be-sorted light source from a reference light source in packaging composition despite substantial similarity in composite light color respectfully output thereby, the to-be-sorted light source being discriminated in spectral content by comparing bend features of a to-be-sorted spectral curve generated from the measured spectral data of the to-be-sorted light source and a reference spectral curve associated with reference spectral data of a reference light source, with respect to a predetermined difference range, the bend features including at least one inflection point,
the to-be-sorted light source thereby discriminated from the reference light source based on packaging using differing compositions of compounds regardless of substantial similarity in composite light color respectively output from the to-be-sorted light source and the reference light source.

* * * * *